US010676432B2

(12) United States Patent
Hanbauer et al.

(10) Patent No.: US 10,676,432 B2
(45) Date of Patent: Jun. 9, 2020

(54) METHODS OF PRODUCING MOLINDONE AND ITS SALTS

(71) Applicant: Supernus Pharmaceuticals, Inc., Rockville, MD (US)

(72) Inventors: Martin Hanbauer, Regensburg (DE); Zarghun Nazir, Linz (AT); Peter Hildebrand, Linz (AT); Attilia Figini, Rancate (CH); Likan Liang, Boyds, MD (US); Tiziano Fumagalli, Pianello del Lario (IT)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 16/107,836

(22) Filed: Aug. 21, 2018

(65) Prior Publication Data
US 2019/0218179 A1 Jul. 18, 2019

Related U.S. Application Data

(60) Continuation of application No. 15/723,515, filed on Oct. 3, 2017, now Pat. No. 10,081,595, which is a continuation of application No. 15/365,566, filed on Nov. 30, 2016, now Pat. No. 9,802,893, which is a continuation of application No. 14/608,262, filed on Jan. 29, 2015, now Pat. No. 9,562,011, which is a division of application No. 13/834,097, filed on Mar. 15, 2013, now Pat. No. 8,957,206.

(60) Provisional application No. 61/701,007, filed on Sep. 14, 2012.

(51) Int. Cl.
*C07D 209/08* (2006.01)
*C07D 295/13* (2006.01)

(52) U.S. Cl.
CPC .......... *C07D 209/08* (2013.01); *C07D 295/13* (2013.01)

(58) Field of Classification Search
CPC .................................................. C07D 209/08
See application file for complete search history.

(56) References Cited

U.S. PATENT DOCUMENTS

| 3,467,755 A | 9/1969 | Schoen et al. |
| 3,491,093 A | 1/1970 | Pachter et al. |
| 4,016,281 A | 4/1977 | Jonas et al. |
| 4,065,453 A | 12/1977 | Finizio |
| 4,707,484 A | 11/1987 | Berger et al. |
| 5,180,834 A | 1/1993 | Wettlaufer et al. |
| 8,957,206 B2 | 2/2015 | Hanbauer |

FOREIGN PATENT DOCUMENTS

| JP | H04-169562 A | 6/1992 |
| JP | 2007-217353 A | 8/2007 |
| WO | WO-2007/074868 A1 | 7/2007 |

OTHER PUBLICATIONS

Achim Porzelle: "Direct Access to Functionalized Cyclic Enones Using Mannich, Morita-Baylis-Hillman and Elimination Reactions," Synthesis, vol. 18, Jan. 1, 2006, pp. 3025-3030, XP055063833.
American Chemical Society; Chemical Abstract Service—Registry No. 1085702-52-8; Copyright 2010.
American Chemical Society; Chemical Abstract Service—Registry No. 15622-65-8; Copyright 2010.
American Chemical Society; Chemical Abstract Service—Registry No. 6116-76-3; Copyright 2010.
Office Action issued in co-pending Japanese Patent Application No. 2015-531913, dated Sep. 27, 2016.
S. Ordzhonikidze All-Union Scientific-Research Institute of Pharmaceutical Chemistry, Moscow; New Method of Synthesizing Molindone and its Analogs; Sep. 1972.
Masaguer et al., "Conformationally restricted butyrophenones with mixed dopaminergic (D2) and serotoninergic (5-HT2A) affinities. Synthesis of 5-aminoethyl and 6-aminomethyl-4-oxotetrahydroindoels as potential atypical antipsychotics", Chemical & Pharmaceutical Bulletin, Jan. 1999, vol. 47, No. 5, pp. 621-632.
Singh, "Synthesis of heterocycles using 4-Oxo-4,5,6,7-tetrahydroindoles as biodynamic molecules", Indian Journal of Chemistry, Section B: Organic Chemistry Including Medicinal Chemistry, Jan. 1982, vol. 21, No. 9, pp. 853-856.
Supplementary Partial European Search Report issued in co-pending EP Application No. 17 18 0165, dated Jan. 24, 2018.
Wu, et al., "Discovery and synthesis of tetrahydroindolone derived semicarbazones as selective Kv1.5 blockers", Bioorganic & Medicinal Chemistry Letters 16, 2006, pp. 5859-5863.
Hauptmann et al., "Hydroxyindoles. 4-Oxo-4,5,6,7-tetrahydroindoles from 1,3-cyclohexanedione and isonitroso carbonyl compounds", Zeitschrift fuer Chemie, 1996, vol. 6, No. 3, p. 107.
Ravina et al., "Butyrophenone analogues: synthesis of 2-methyl-3-ethyl-5-aminoethyl-4,5,6,7-tetrahydroindol-4-ones, and their affinities for D1, D2 and 5-HT2A receptors", Bioorganic & Medicinal Chemistry Letters, 1995, vol. 5, No. 6, pp. 579-584.

*Primary Examiner* — Shawquia Jackson
(74) *Attorney, Agent, or Firm* — Foley & Lardner LLP

(57) ABSTRACT

The present invention is directed towards novel methods of synthesis of molindone, synthesis of the intermediates of molindone, and high-purity compositions of molindone. In particular, the invention relates to the methods of synthesis of molindone through the Mannich reaction.

13 Claims, No Drawings

METHODS OF PRODUCING MOLINDONE AND ITS SALTS

CROSS-REFERENCE TO RELATED APPLICATIONS

This application is a Continuation Application of U.S. patent application Ser. No. 15/723,515, filed Oct. 3, 2017, which is a Continuation Application of U.S. patent application Ser. No. 15/365,566, filed Nov. 30, 2016, now U.S. Pat. No. 9,802,893, which is a Continuation Application of U.S. patent application Ser. No. 14/608,262, filed Jan. 29, 2015, now U.S. Pat. No. 9,562,011, which is a Division Application of U.S. patent application Ser. No. 13/834,097, filed on Mar. 15, 2013, now U.S. Pat. No. 8,957,206, which claims benefit of U.S. Provisional Application 61/701,007, filed on Sep. 14, 2012, the contents of each of which are incorporated in its respective entirety.

FIELD

Described herein are methods for improved production of active pharmaceutical ingredients ("APIs"} such as molindone, including methods having increased yields and producing decreased amounts of impurities. This disclosure further describes and characterizes salts of APIs such as molindone hydrochloride, including novel polymorphs thereof.

BACKGROUND

Molindone is 3-Ethyl-6,7-dihydro-2-methyl-5-(morpholinomethyl)indol-4(5H)-one (CAS #7416-34-4). The chemical formula of molindone is represented below:

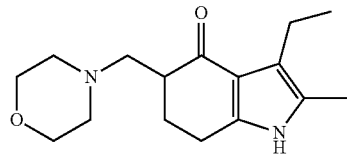 [SMILES: CCc1c(C)[nH]c2c1C(=O)C(CN1CCOCC1)CC2]

Molindone is a weak base, exhibiting greater solubility in acidic to slightly acidic media than in neutral to slightly alkaline pH values (i.e., the physiologic pH range of the gastro intestinal tract). As a weakly basic drug, molindone is typically used in formulations in the form of a salt. Various prior art methods of manufacturing molindone, such as disclosed in U.S. Pat. Nos. 3,491,093 and 3,646,042, are known. However, the prior art methods may result in a drug product that does not meet the modem purity requirements. Thus, what are needed in the art are methods for producing molindone while reducing or eliminating the formation of certain impurities.

SUMMARY OF THE INVENTION

Provided herein are new and improved methods of manufacture of molindone and its various salts, as well as molindone-related compounds, such as novel intermediates. In particular, the methods herein provide a substantially pure API of molindone salts, such as hydrochloride, while avoiding undesirable impurities. The methods further provide for synthesizing, separating, identifying, and characterizing novel polymorphs of molindone. Further provided are methods of identification and characterization and methods for synthesis of novel intermediates of molindone, as well as methods for synthesis of exemplary metabolites and precursors of metabolites of molindone.

In an exemplary embodiment, the invention provides a substantially pure composition suitable for use as an active pharmaceutical ingredient, the composition consisting essentially of molindone or a pharmaceutically acceptable salt thereof and comprising less than about 1.5 μg of any genotoxic impurity per expected maximum human daily dose. In another exemplary embodiment, the composition comprises less than 0.5 μg of any genotoxic impurity per expected maximum human daily dose.

In another embodiment, the invention provides a method of manufacturing molindone through the reaction of 2-methyl-3-ethyl-4-oxo-4,5,6,7-tetrahydroindole (SUMO-2) with bismorpholinomethane.

In yet another embodiment, 2-methyl-3-ethyl-4-oxo-4,5,6,7-tetrahydroindole (SUMO-2) is produced by reacting 2,3-pentanedione-2-oxime and 1,3-cyclohexanedione.

In another embodiment, SUMO-2 is produced by reacting 2-amino-pentan-3-one with 1,3-cyclohexanedione. In a further embodiment, 2-amino-pentan-3-one is generated by reducing 2,3-pentanedione-2-oxime.

In a further embodiment, 2,3-pentanedione-2-oxime (SUMO-1) is produced through the reaction of 2,3-pentanedione with hydroxylamine hydrochloride.

In a specific embodiment, the invention provides a method of manufacturing molindone through a 3-step process, wherein in the 1st step 2,3-pentadione is reacted with hydroxylamine hydrochloride to produce 2,3-pentanedlone-2-oxime (SUMO-1); in the 2nd step 2,3-pentanedione-2-oxime and 1,3-cyclohexanedione are reacted to produce 2-methyl-3-ethyl-4-oxo-4,5,6,7-tetrahydroindole (SUMO-2); and in the 3rd step 2-methyl-3-ethyl-4-oxo-4,5,6,7-tetrahydrolndoie reacts with bismorphollnomethane to produce molindone (SUMO-3).

In yet another embodiment, the invention provides a method of manufacturing of a molindone salt by producing molindone base and reacting it with an acid.

In a further embodiment, various polymorphic forms of a molindone salt are prepared.

In yet a further embodiment, the invention provides a method of manufacturing molindone through a 5-step process, wherein in the 1st step 2,3-pentanedione is reacted with hydroxylamine hydrochloride to produce 2,3-pentanedione-2-oxime (SUMO-1); in the 2nd step 2,3-pentanedione-2-oxime and 1,3-cyclohexanedione are reacted to produce 2-methyl-3-ethyl-4-oxo-4,5,6,7-tetrahydroindole (SUMO-2); In the 3rd step 2-methyl-3-ethyl-4-oxo-4,5,6,7-tetrahydroindole reacts with bismorpholinomethane to produce molindone (SUMO-3); in the 4th step molindone is converted into a molindone salt; and in the 5th step the molindone salt is purified/recrystallized, and, optionally, various polymorphic forms of molindone salt are prepared.

Further, the invention provides a method of manufacturing of the molindone-related compounds.

The present invention relates to a process for preparing a compound SUMO-3, which includes the step of reacting (SUMO-2) with bismorpholinomethane. in one aspect of the present invention, the process includes the steps of removing methylene SUMO-2 by filtration under acidic conditions, adsorbing oligomeric compounds on charcoal, and filtering and crystallizing SUMO-3 free base from a solvent. Without limitation, the solvent can be selected from ethanol, methanol, isopropanol, butanol, acetone, ether, methyl t-butyl ether, nitromethane, ethyl acetate, toluene or combinations thereof. In one embodiment, either of the processes as set forth above further includes a step of formation and crystallization of a salt of SUMO-3. Without limitation, the salt can be molindone hydrochloride, molindone sulfate, molindone phosphate, molindone monohydrogenphosphate, molindone dihydrogenphosphate, molindone bromide, molindone iodide, molindone acetate, molindone propionate, molindone decanoate, molindone caprylate, molindone formate, molindone oxalate, molindone malonate, molindone succinate, molindone fumarate, molindone maleate, molindone citrate, molindone lactate, molindone tartrate, molindone methanesulfonate, or molindone mandelate. In another embodiment of any of the processes set forth herein, the amount of the residual isomer-SUMO-3 is less than 0.2%.

In another embodiment of any of the processes set forth herein, the compound SUMO-2 is prepared by reacting SUMO-1 with 1,3-cyclohexanedione. In a further embodiment, the compound SUMO-2 is prepared by reacting SUMO-1 with 1,3-cyclohexanedione in the presence of a catalyst Exemplary catalysts include palladium on carbon (Pd/C) or Raney nickel.

In yet another embodiment of the present invention, the compound SUMO-2 is prepared by reacting SUMO-1 with 1,3-cyclohexanedione in the presence of zinc (Zn) in acetic acid. The Zn can be present in the form of a powder. In a further exemplary embodiment, the powder can have a particle size of from about 2 microns to about 50 microns. In some embodiments, the SUMO-1 can be subjected to hydrogenation conditions prior to the addition of 1,3-cyclohexanedione. In a further exemplary embodiment, hydrogenation conditions include the use of a hydrogenation agent such as Zn/HOAG or a catalyst such as Pd/C or Raney nickel.

The process in accordance with embodiments of the present invention as set forth herein, may be initiated at a first temperature of from about 15° C. to about 40° C. in one embodiment, the reaction temperature of the process may be further raised to a second temperature of from about 80° C. to about 110° C.

In another aspect of the present invention, compound SUMO-1 is prepared by reacting 2,3-pentadione with hydroxylamine hydrochloride in the presence of a base. Without limitation, the base can be LiOH, NaOH, KOH, $Li_3CO$, $K_2CO_3$, $Na_2CO_3$, $NaHCO_3$, or combinations thereof. In at least one embodiment the preparation of SUMO-1 is carried out at a pH of from 8 to 9 to optimize regioselectivity.

In at least one embodiment, preparation of SUMO-1 can be carried out in such a way that the ratio of SUMO-1/SUMO-1 isomer is at least 5:1.

Another aspect of the present invention relates to a substantially pure composition including molindone or pharmaceutically acceptable salts thereof, wherein the composition includes less than 1.5 µg of any genotoxic impurity per expected maximum human daily dose.

There have thus been outlined, rather broadly, exemplary features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that equivalent constructions insofar as they do not depart from the spirit and scope of the present invention, are included in the present invention.

For a better understanding of the invention, its operating advantages and the specific objects attained by its uses, reference should be had to the accompanying drawings and descriptive matter which illustrate preferred embodiments of the invention,

DETAILED DESCRIPTION

As used above and throughout the description of the invention, the following terms, unless otherwise indicated, shall be defined as follows:

The term "equivalent" or "eq." refers to the molar equivalent of the subject compound.

The term "neat" means that the subject acid or base is undiluted with a solvent.

The term "basifying agent" means any compound which, via its presence in a composition, increases the pH of this composition by at least 0.05 pH unit, such as at least 0.1 pH unit.

Provided herein are new and improved methods of manufacture of substantially pure compositions of molindone and pharmaceutically acceptable salts and polymorphs thereof with improved control of impurities to thereby provide materials suitable for pharmaceutical applications.

For the sake of convenience and without putting any limitations thereof, the methods of manufacture of molindone have been separated into several independent steps, each independent step being disclosed herein in a multiplicity of non-limiting and independent embodiments. These independent steps comprise steps 1-3 and optional steps 4 and 5, wherein in the 1st step 2,3-pentadione is reacted with hydroxylamine hydrochloride to produce 2,3-pentanedione-2-oxime (SUMO-1); in the 2nd step 2,3-pentanedione-2-oxime and 1,3-cyclohexanedione are reacted to produce 2-methyl-3-ethyl-4-oxo-4,5,6,7-tetrahydroindole (SUMO-2); and in the 3rd step 2-methyl-3-ethyl-4-oxo-4,5,6,7-tetrahydroindole reacts with bismorpholinomethane to produce molindone (SUMO-3). In the 4th step molindone is converted into a molindone salt; and in the 5th step the molindone salt is purified/recrystallized, and various polymorphic forms of the molindone salt are prepared.

The above-mentioned steps will be considered below in more details.

SUMO-3 Preparation Step

It was unexpectedly discovered that molindone (SUMO-3) may be prepared through the reaction of SUMO-2 with a Mannich reagent.

In one embodiment, the Mannich reagent used to prepare SUMO-3 is bismorpholinomethane.

The synthesis proceeds according to the Reaction 1:

Reaction 1:

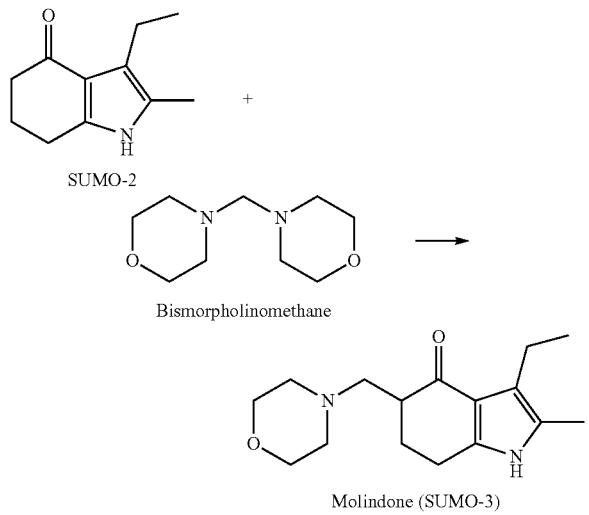

The source of bismorpholinomethane useful for Reaction 1 is not limited. Bismorpholinomethane of sufficient purity may be acquired from a commercial source, or may be synthesized in situ. In one specific embodiment bismorpholinomethane is synthesized in situ according to the Reaction 2:

Reaction 2:

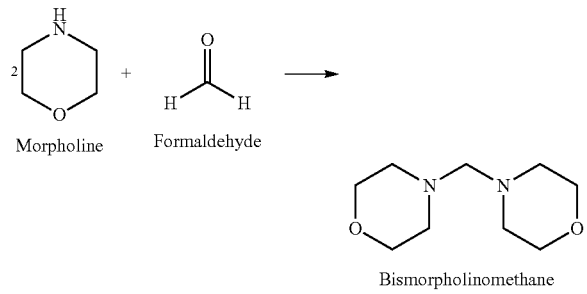

The Mannich reagent (e.g., bismorpholinomethane) is used for the reaction in the amounts of from 1 eq to 4 eq. In one embodiment, the amount of the Mannich reagent (e.g., bismorpholinomethane) varies from 1 eq to 2 eq. In another embodiment, the amount is between 2 eq and 4 eq.

The Reaction 1 is advantageously conducted in the presence of an acid. Representative acids may be selected from hydrogen chloride, acetic acid, formic acid, sulfuric acid, nitric acid, phosphoric acid, trifluoroacetic acid, and combinations thereof; and may be used in a wide range of amounts, starting from 1 eq to up to a neat media to form a solution of the reaction mixture in the neat acid.

Further, a solvent may be added to the reaction mixture. The solvent may be selected from methanol, ethanol, propanol, isopropanol, butanol, pentanoi, ethylene glycol, ethoxyethanol, methoxyethanol, 1,4-dioxane, toluene, xylene, tetrahydrofuran, dichloromethane, benzene, and combinations thereof.

Elevated temperature is used to facilitate the reaction. In at least one embodiment, the reaction is conducted at the temperature of from 40° C. to 110° C. In alternative embodiments, the reaction is conducted at the temperature of from 50° C. to 90° C.

The addition sequence, the ratio of the reagents, and the reaction conditions for Reaction 1 may be controlled to obtain maximum yield, improve the purity of the product or to control the side reactions that lead to the formation of impurities.

In one embodiment, the reaction is conducted at a constant temperature of from 60° C. to 110° C. In alternative embodiments, the reaction is conducted at a constant temperature of from 70° C. to 100° C.

In another embodiment, the reaction is initiated at the lower end of the temperature range, and then the temperature is raised during the reaction. For example, the temperature may be raised to 65° C.-100° C. during the reaction.

In a further embodiment, the whole amount of the Mannich reagent (e.g., bismorpholinomethane) is pre-charged at the initiation of the reaction.

In yet another embodiment, the Mannich reagent is added in a stepwise manner with the initial amount charged at the start of the reaction, followed by the additional amount(s) added after some period of time. The timing of the second and further additions of the Mannich reagent may vary but is typically selected from the period of time of between 1 hour and 4 hours. The initial amount of the reagent constitutes from 50% to 90% of the total amount of the reagent; or from 60% to 80%. In some embodiments of the present invention, a Mannich reagent is added in a continuous manner over a period of time. Exemplary time periods for continuous addition of a Mannich reagent include from about 1 hour to about 4 hours.

In an additional embodiment for producing molindone with fewer impurities, the reaction is advantageously initiated at the lower end of the temperature range with the initial amount(s) of the Mannich reagent (e.g., bismorpholinomethane), and followed by temperature increase and the addition of the reagent as described in the previous embodiment.

The product of Reaction 1 is further purified. In one embodiment, the acidic solution containing the products of Reaction 1 is treated with water to dissolve the molindone followed by filtration. Additional acid may be added to increase the solubility of the molindone free base in the aqueous phase. Additional acid in this embodiment can be selected from hydrogen chloride (HCL), sulfuric acid ($H_2SO_4$), nitric acid ($HNO_3$), or phosphoric acid ($H_3PO_4$).

Upon completion of the Reaction 1, the aqueous acidic solution containing the reaction products is treated with a base to obtain a pH of more than 7 to precipitate molindone (SUMO-3) free base. The bases used for molindone base precipitation may be selected from ammonia, carbonates, bicarbonates, hydroxides, and combinations thereof. The base may be used in the form of a solution or in neat form. In a specific embodiment, an adsorbent can be additionally used during the base treatment step to facilitate the filtration of the molindone precipitate and to remove impurities. The adsorbent may be selected from charcoal, zeolite, silicates, and celite.

The precipitated molindone base may be further dissolved and re-crystallized. Exemplary solvents useful for the re-crystallization include ethanol, methanol, isopropanol, butanol, acetone, ether, methyl t-butyl ether, nitromethane, ethyl acetate, toluene and combinations thereof.

Potential impurities that could result from Reaction 1 include:

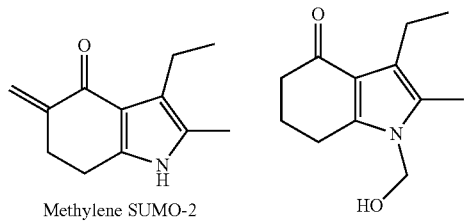

Methylene SUMO-2

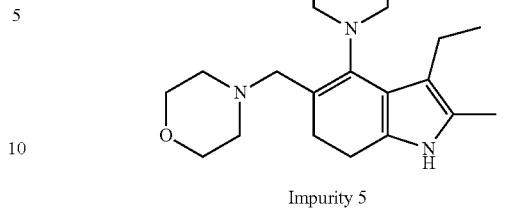

Hydroxymethyl SUMO-2

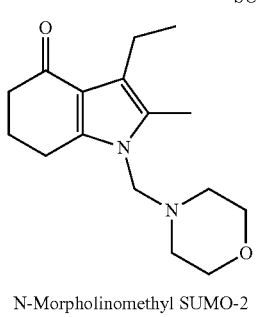

N-Morpholinomethyl SUMO-2

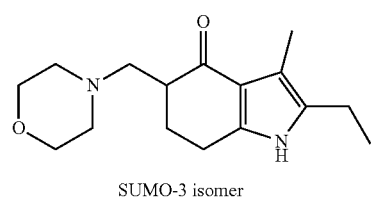

SUMO-3 isomer

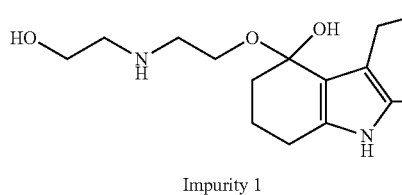

Impurity 1

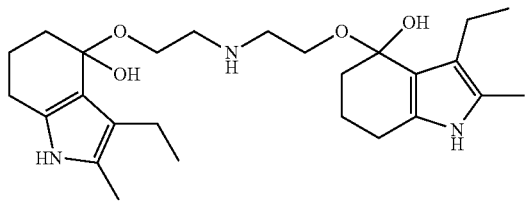

Impurity 2

Impurity 3    Impurity 4

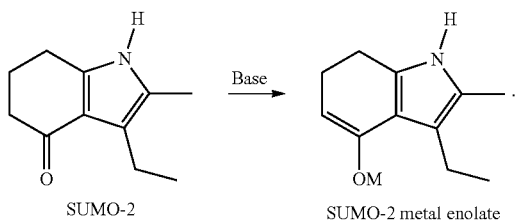

Impurity 5

The novel reaction scheme of STEP 1 minimizes, or excludes, the formation of one or more of the above-listed impurities.

In an alternative embodiment, SUMO-3 may be prepared through the novel reaction process according to Reaction 3, wherein morpholine is used as a Mannich reagent. The Reaction 3 comprises steps 3a-3d and proceeds through the formation of two novel intermediates, formyl SUMO-2 and enamine of the formyl SUMO-2:

Reaction 3

3a

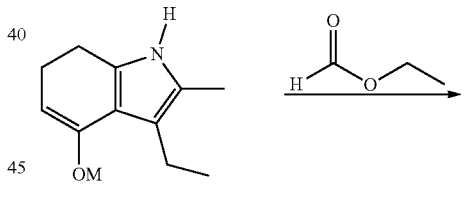

SUMO-2    SUMO-2 metal enolate

3b

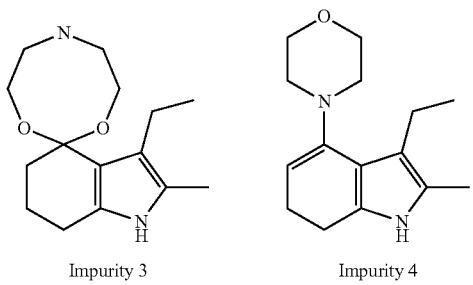

SUMO-2 metal enolate

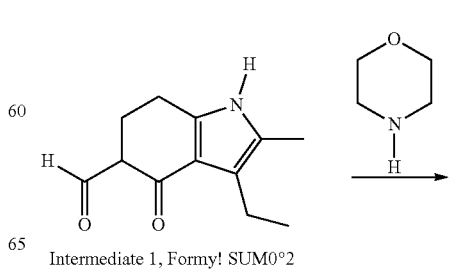

Intermediate 1, Formyl SUMO-2

3c

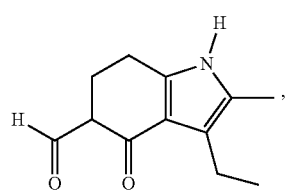

Intermediate 1, Formyl SUMO-2

-continued

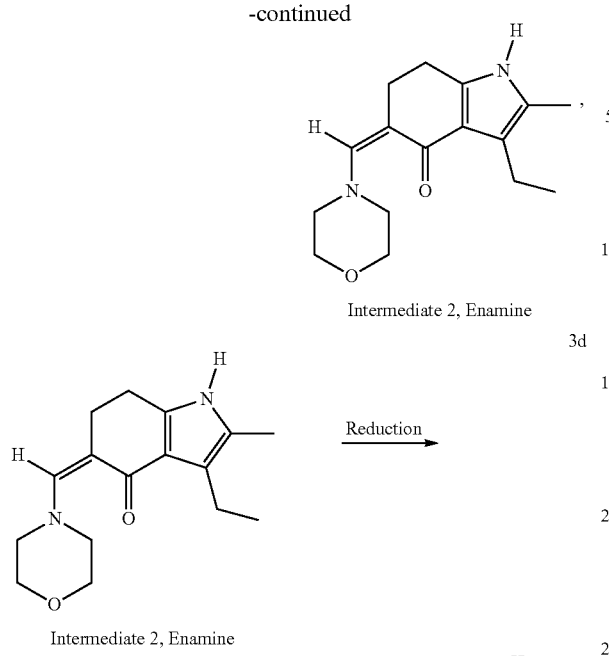

SUMO-2 Preparation Step

While methods of preparation of SUMO-2 that are used to produce molindone according to the practice of the instant invention are known in the art; it was unexpectedly discovered that SUMO-2 may be advantageously produced through the reaction of SUMO-1 and 1,3-cyclohexanedione under hydrogenating conditions in the presence of a catalyst. The reaction proceeds according to the following Reaction 4 scheme:

Reaction 4:

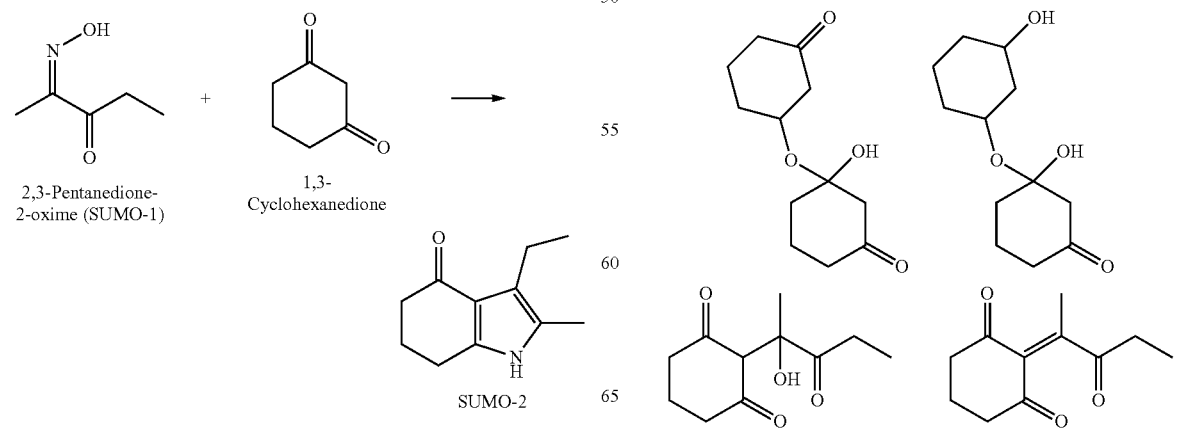

It was further discovered that SUMO-2 can be advantageously produced with fewer impurities by first producing an intermediate of the following formula, followed by producing SUMO-2 in a stepwise manner.

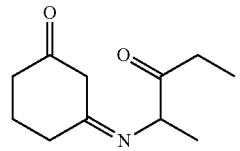

SUMO-2 Acyclic Intermediate

In one embodiment, Reaction 4 is carried out as a single-stage reaction without accumulation of the intermediate. Beneficially, the reaction is carried out in the presence of an acid. The acid may be an inorganic or organic acid selected from hydrochloric acid, sulfuric acid, nitric acid, formic acid, acetic acid, trifluoroacetic acid, and combinations thereof. In one variation, the acid is acetic acid.

The following possible by-products were identified in the reaction of this embodiment:

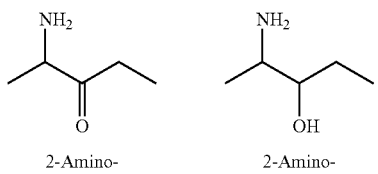

2-Amino-pentan-3-one     2-Amino-pentan-3-ol

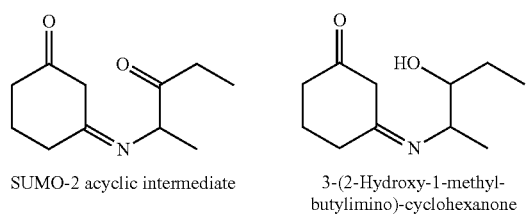

SUMO-2 acyclic intermediate     3-(2-Hydroxy-1-methyl-butylimino)-cyclohexanone

Potential impurities in SUMO-2

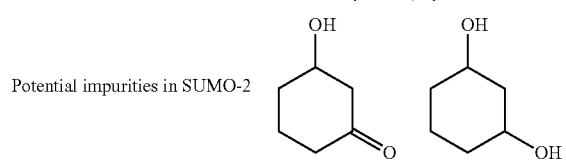

-continued

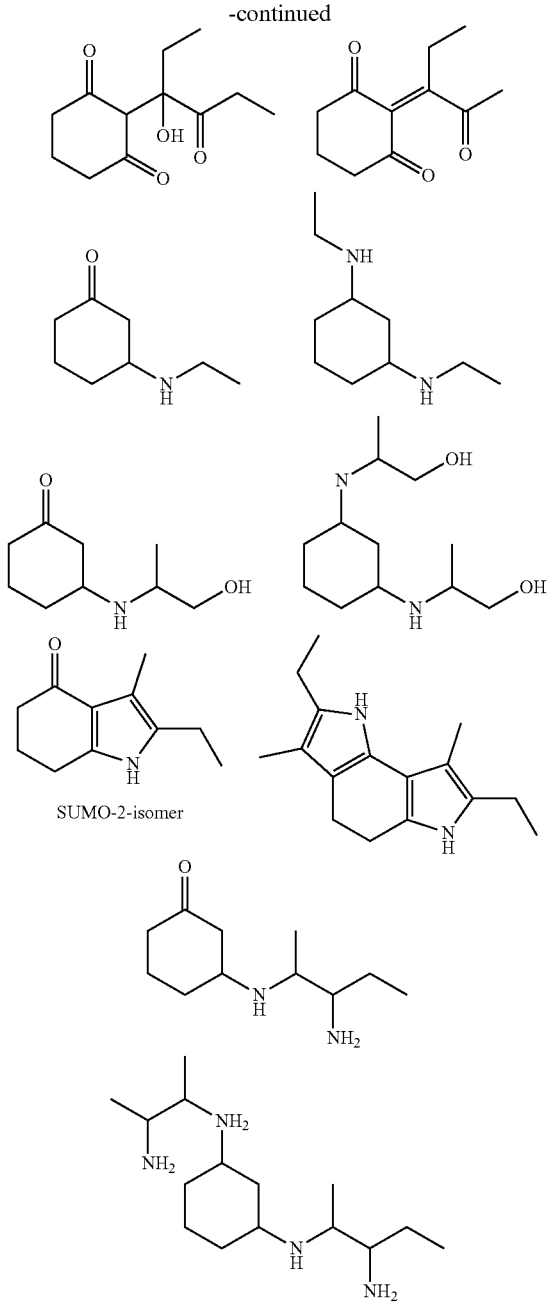

SUMO-2-isomer

In another embodiment, Reaction 4 is carried out as a two-stage reaction, wherein the first stage of the reaction is a hydrogenation stage, and the second stage is a cyclization stage.

The hydrogenation stage is performed under low to moderate hydrogen pressure in the presence of a catalyst An acid can be used advantageously in the hydrogenation stage to shorten the reaction time. The hydrogen pressure may be set between 1-5 bar. The acid useful for the practice of this embodiment may be selected from HCl, sulfuric acid, acetic acid, trifluoroacetic acid, nitric acid and combinations thereof. In one specific example, the acid is acetic acid. In another example, the acid comprises acetic acid mixed with a solvent, such as ethyl acetate, ethanol, methanol, benzene, toluene, xylene and combinations thereof.

In the first variation of this embodiment, the reactants (SUMO-1 and 1,3-cyclohexanedione) are pre-charged, and the hydrogenation stage is carried out at the lower temperature in the presence of a catalyst. In this variation, the SUMO-2 intermediate is formed at lower temperature. The hydrogenation stage is then followed by the cyclization stage carried out at higher temperature. The temperature for the hydrogenation stage may be from 15° C. to 40° C. In an alternative embodiment, the hydrogenation stage takes place at the temperature of 15° C.-25° C. The temperature for the cyclization stage is from 70° C. to 110° C., for example, from 70° C. to 90° C., or from 90° C. to 100° C., or from 100° C. to 110° C.

In the second variation of the embodiment, the temperature protocol corresponds to that of the first variation, but hydrogenation stage proceeds in the absence of 1,3-cyclohexanedione, which is charged later at the high temperature cyclization phase. In this variation, 2-amino-pentan-3-one is advantageously produced first. It was unexpectedly discovered that the selectivity of Reaction 4 and the yield and purity of SUMO-2 are improved by subjecting only SUMO-1 to the reduction conditions followed by the addition of 1,3-cyclohexanedione at the later stage.

In one approach, the hydrogenation stage of Reaction 4 requires the presence of a catalyst, such as Raney nickel catalyst, $PtO_2$ and Pd catalyst.

In one embodiment of Reaction 4, the catalyst comprises Raney nickel catalyst. The catalyst is used in this embodiment in the amounts of from 0.01 g/g to 0.4 g/g, and more specifically, of from 0.05 g/g to 0.3 g/g.

In another embodiment of Reaction 4, the catalyst comprises Pd/C catalyst.

The catalyst is used in this embodiment in the amounts of from 0.01 g/g to 0.2 g/g, and more specifically, of from 0.05 g/g to 0.15 g/g.

Optionally, the used catalyst is removed from the reaction mixture after the hydrogenation step to prevent the formation of by-products.

Alternatively, the hydrogen necessary for the hydrogenation stage of Reaction 4 may be generated in situ by the addition of zinc powder in the presence of acetic acid. In this case, the reaction may be carried out with all reactants being charged at the beginning at lower temperature followed by temperature increasing protocol; or with SUMO-1, zinc and the acid charged at the reduction stage, and with cyclohexanedione charged only at the cyclization stage, with or without temperature increasing protocol. Optionally, the residual zinc and zinc acetate are filtered out after the hydrogenation.

The particle size for the zinc powder is in the range of from 2μ to 50μ. In an alternative embodiment, the particle size for the zinc powder is in the range of from 5μ to 20μ.

In one additional embodiment, SUMO-2 can be advantageously produced with fewer impurities by reacting 1,3-cyclohexanedione with 2-amino-pentan-3-one of the following structure, which can be obtained by reducing 2,3-pentanedione-2-oxime (SUMO-1),

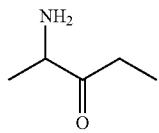

2-Amino-pentan-3-one

By way of a non-limiting example, 2-amino-pentan-3-one can be obtained by reducing 2,3-pentanedione-2-oxime (SUMO-1).

In order to remove impurities and undesired isomers, the product of the Reaction 4, SUMO-2, is optionally subjected to at least one re-crystallization cycle.

The novel reaction schemes for the preparation of SUMO-2 minimize, or preclude, the formation of one or more of the above-listed impurities.

SUMO-1 Preparation Step

Methods of preparation of SUMO-1 used for the preparation of SUMO-2 are known in the art. SUMO-1 may be prepared, for example, through the reaction of 2,3-pentanedione with hydroxylamine hydrochloride in the presence of a base (Reaction 5).

Reaction 5:

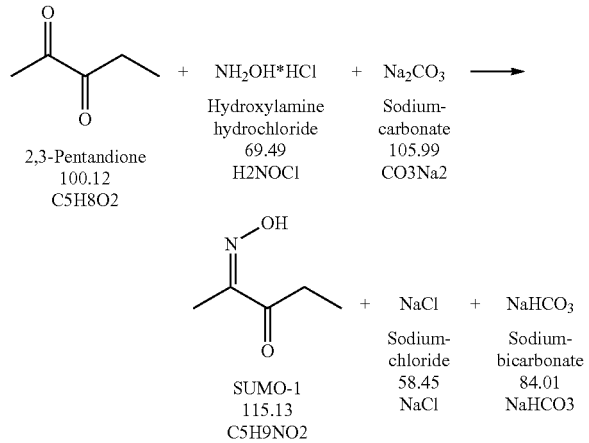

Generally, regioselectivity of the reaction of 2,3-pentanedione with hydroxylamine to SUMO-1 is not high, resulting in the formation of the SUMO-1 isomer 2,3-pentanedione-3-oxime and 2,3-pentanedione-2,3-dioxime, along with the desired product 2,3-pentanedione-2-oxime SUMO-1.

It was unexpectedly discovered that the regioselectivity of this reaction can be optimized through the careful control of reaction conditions, such as the nature and amount of the basifying agent, pH, solvents, temperature and a dosing sequence.

The process of Reaction 5 may be carried out at pH values ranging from 4.5 to 9.5.

In one embodiment, Reaction 5 takes place at pH values ranging from 4.5 to 8. In another embodiment, the reaction takes place at pH values in the range of from 8 to 9.5.

The base, useful for establishing the necessary pH, may be selected from lithium hydroxide (LiOH), sodium hydroxide (NaOH), potassium hydroxide (KOH), lithium carbonate ($Li_2CO_3$), potassium carbonate ($K_2CO_3$), sodium carbonate ($Na_2CO_3$), and combinations thereof. The base may be employed in the amounts of from 1.0-3.0 eq, for example, in the amount of 1.05-1.5 eq or 1.05-2.0 eq.

In one embodiment of SUMO-1 preparation, the base is selected from NaOH, KOH and combinations thereof. In another embodiment, the base is selected from $Li_2CO_3$, $K_2CO_3$, $Na_2CO_3$, and combinations thereof.

In yet another embodiment, the base is $Na_2CO_3$, which may be used in the amounts of from 1 to 3 equivalents. In one variation of this embodiment, sodium carbonate was used in the amount of about 1.0 equivalent. In a further variation of this embodiment, sodium carbonate was used in the amounts of 1.1 equivalents. In yet another variation, sodium carbonate was used in the amount of 1.2 equivalents.

As it was discovered that the lower temperature of the reaction leads to better selectivity, Reaction 5 advantageously takes place at a temperature of from 5° C. to 20° C. In one embodiment, the reaction takes place at a temperature of from 5° C. to 0° C. In another embodiment, the temperature is from 0° C. to −15° C. In yet another embodiment, the temperature is set to be from −5° C. to −10° C.

Further, an addition of an anti-freezing agent to lower the freezing point of the solution is beneficial for the reaction. The anti-freezing agent can be selected from the alkaline and alkaline earth metal halides, such as sodium chloride (NaCl), potassium chloride (KCL), calcium chloride ($CaCl_2$), magnesium chloride ($MgCl_2$), and the like.

The solvents useful for the reaction of Reaction 5 are selected from the group consisting of water, methyl tertiary butyl ether (MTBE), methanol, ethanol, isopropanol, tetrahydrofuran (THF), acetonitrile, pyridine, ethyl ether, acetic acid and combinations thereof. The following solvents may be additionally added to provide anti-freezing properties: glycerol, ethylene glycol, propylene glycol, diethylene glycol and combinations thereof.

A high yield of SUMO-1, above 90%, can be obtained through realizing the above-described embodiments of Reaction 5, with reduced amounts of impurities generated in the product.

The following compounds were identified as potential by-products resulting from Reaction 5:

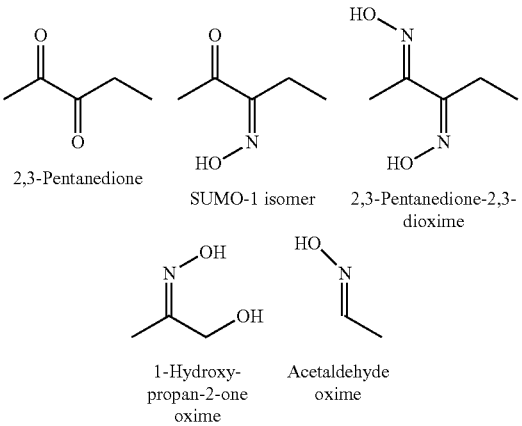

The novel reaction scheme of this step minimizes, or precludes, the formation of one or more of the above-listed impurities.

In alternative embodiments, the ratio of SUMO-1 to SUMO-1 isomer was determined to be above 5, above 6, or above 6.5.

In one embodiment of SUMO-1 preparation, the levels of the 2,3-pentadione-2,3-dioxime impurities are not exceeding 0.2%. In alternative embodiments, the levels of the 2,3-pentadione-2,3-dioxime impurities are not exceeding 0.1%.

Purified molindone (SUMO-3) free base produced according to the practice of the instant invention may be converted into a molindone salt, such as chloride, sulfate, phosphate, monohydrogenphosphate, dihydrogenphosphate, bromide, iodide, acetate, propionate, decanoate, caprylate, formate, oxalate, malonate, succinate, fumarate, maleate, citrate, lactate, tartrate, methanesulfonate, mandelate and the like. The salts may be prepared through the reaction of molindone base with the acid in a warm alcoholic solution, followed by cooling. The solvent useful for the salt formation may be selected from MTBE, methanol, ethanol, isopropanol, THF, acetonitrile and combinations thereof, which can be combined with ethyl acetate, hexane, heptane, benzene, toluene, cyclohexane, or water. In at least one embodiment, the temperature of the alcoholic solution for crystallization is in the range of from −20° C. to 25° C.

In one specific, but non-limiting, embodiment the salt is molindone HCl.

The invention further provides a substantially pure composition consisting essentially of molindone or pharmaceutically acceptable salts thereof. In varying embodiments, the term "substantially pure" refers to compositions containing essentially only the active pharmaceutical ingredient and less than about 1.5 µg (or less than about 0.5 µg) of any genotoxic impurity per expected maximum human daily dose, and they are therefore suitable for use in the preparation of pharmaceutical dosage forms intended for human consumption. Further, in varying embodiments, the term "substantially pure" refers to compositions containing at least about 98% (or alternatively at least about 99%, or at least about 99.5%) by weight of the active pharmaceutical ingredient. Even further, the term "substantially pure" refers to compositions containing less than about 0.1% of any single unknown impurity. In this context, an "impurity" refers to reaction side-products or reaction intermediates or residual reagents or undesirable products thereof, which may remain in the active pharmaceutical ingredient after synthesis. In varying embodiments, the "substantially pure" compositions referred to herein contain only the inventive active pharmaceutical ingredient as the principal or the sole physiologically or pharmacologically active component.

As used herein, the term "genotoxic" refers to compounds or substances that are suspected to, or have demonstrated to, induce genetic mutations, chromosomal breaks and/or chromosomal rearrangements.

By way of example, a "substantially pure" composition of molindone (or a pharmaceutically acceptable salt thereof) contains less than about 1.5 µg, less than about 1.0 µg, and less than about 0.5 µg of any genotoxic impurity per maximum daily molindone dose in humans.

In another embodiment, the invention provides novel compounds according to the following formulas:

NC-1
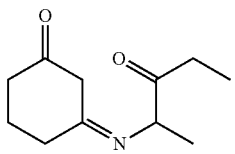

NC-2
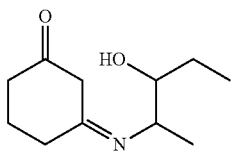

NC-3
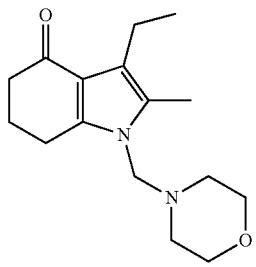

NC-4
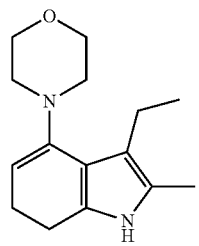

NC-5
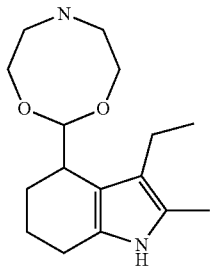

NC-6
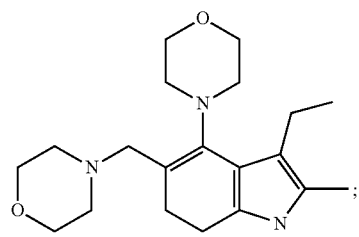

NC-7
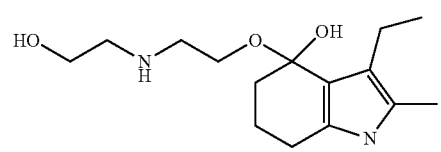

NC-8
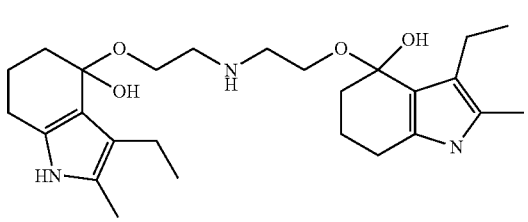

NC-9
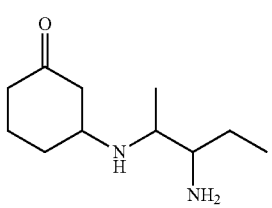

NC-10

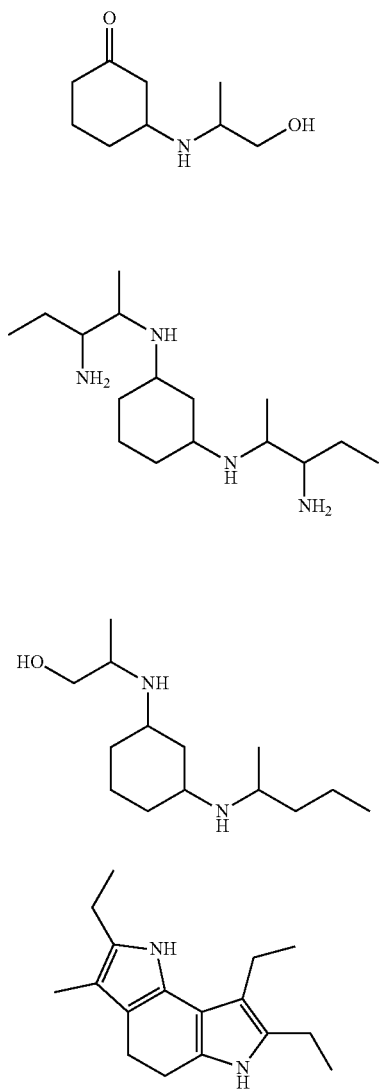

In the additional embodiment of the invention, the new and improved methods of manufacture of molindone disclosed above can be used to prepare molindone-related compounds by using corresponding SUMO-1 analogs and bismorpholinomethane analogs. The preparation is exemplified in reactions 6, 7, 8 and 9, wherein R1, R2, R3, R4, and R5 are selected from —H, —OH, alkoxy, alkyl, or substituted alkyl groups.

Reaction 6:

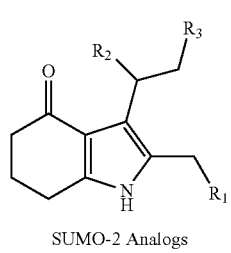 +

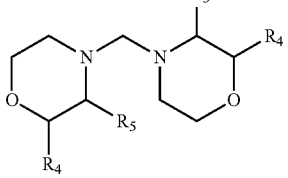

Bismorpholinomethane Analogs

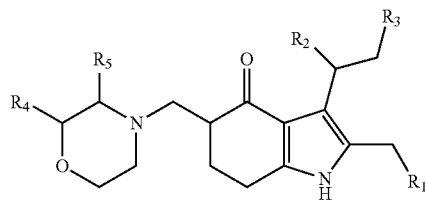

Molindone Analogs

Reaction 7:

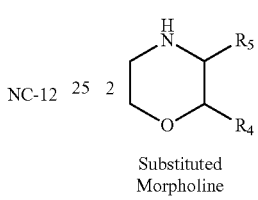 + 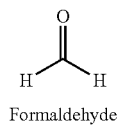

Substituted Morpholine    Formaldehyde

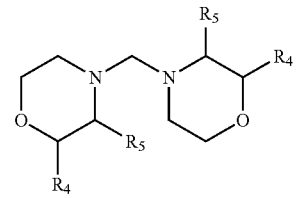

Bismorpholinomethane Analogs

Reaction 8:

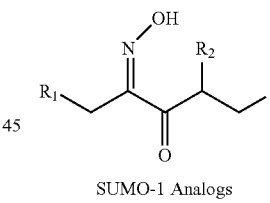 + 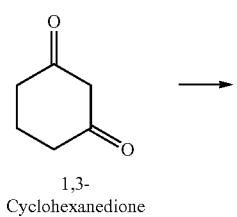

SUMO-1 Analogs    1,3-Cyclohexanedione

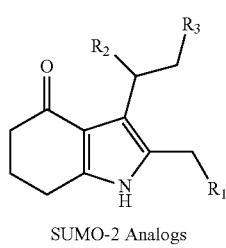

SUMO-2 Analogs

Reaction 9:

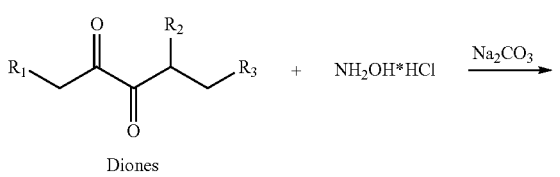

Diones

-continued

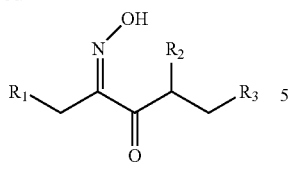

SUMO-1 Analogs

Examples of the molindone analogs that can be prepared by reactions 6, 7, 8 and 9 include, but are not limited to:

MA1

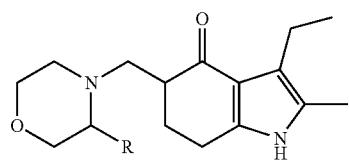

R = —OH,
alkoxy, alkyl, substituted alkyl

MA-2

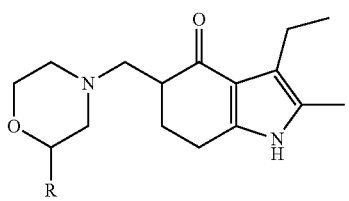

R = —OH,
alkoxy, alkyl, substituted alkyl

MA-3

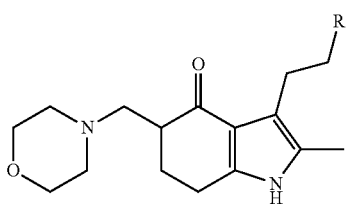

R = —OH,
alkoxy, alkyl, substituted alkyl

MA-4

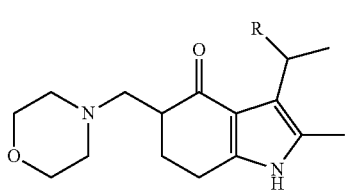

R = —OH,
alkoxy, alkyl, substituted alkyl

MA-5

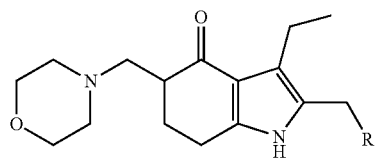

R''' —OH,
alkoxy, alkyl, substituted alkyl

Further, hydroxymethyl SUM02 of the formula below,

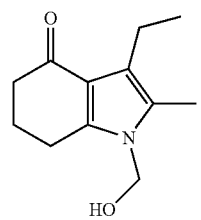

Hydroxymethyl SUMO-2 can be prepared by reacting SUMO-2 with formaldehyde, and used with the bismorpholinomethane analogs in combination with the methods disclosed herein to produce molindone analogs with the following formula:
MA-6:

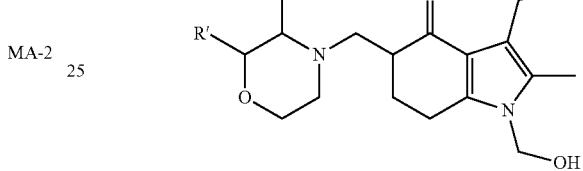

R', R'' = —H, —OH, alkoxy, alkyl, substituted alkyl

EXAMPLES

The invention now being generally described, it will be more readily understood by reference to the following examples which are included merely for purposes of illustration of certain aspects and embodiments of the present invention, and are not intended to limit the invention.

Examples for SUMO-1 Preparation Step

Example 1. Preparation of SUMO-1

2,3-pentanedione and hydroxylamine hydrochloride were dissolved separately in water/EtOH (3/1; w/w %). Then the solution of hydroxylamine hydrochloride was added to the solution of 2,3-pentanedione at predetermined pH and low or room temperature. The pH-value of the reaction-mixture was adjusted with 1N NaOH. The final concentration of 2,3-pentanedione in the reaction-mixture was ~3.5 w %. After the reaction, the solution was extracted with MTBE.

The same procedure was repeated at various temperatures and pH values. The results are presented in Tables 1 and 2.

TABLE 1

| Effect of pH on SUMO-1 Yield (T = 3° C.) | | |
|---|---|---|
| Experiment # | pH | Yield (%)* |
| PER-3131-1 | 4.5 | 57.9 |
| PER-3132-1 | 6.5 | 75.7 |
| PER-3130-1 | 8.5 | 81.1 |

*As area % in HPLC

TABLE 2

Effect of Temperature on SUMO-1 Yield (pH = 8.5)

| Experiment # | Temperature (° C.) | Yield (%)* |
|---|---|---|
| PER-3129-1 | Room temperature | 68.2% |
| PER-3130-1 | 3° C. | 81.1% |
| PER-3137 | −5° C. | 82.2% |

*As area % in HPLC

Example 2. Preparation of SUMO-1

An aqueous solution of sodium carbonate (ca. 12% w/w) was cooled to 0° C., followed by dosing of an aqueous solution of hydroxylamine hydrochloride (ca. 20% w/w). Then an ethanolic solution of pentandione (50 w %) was dosed at 0° C. over 2 hours.

After aging for 1 hour at 0° C., the reaction mixture was warmed to room temperature and MTBE was added to dissolve the partially precipitated partially oily product (6 g MTBE/g pentandione). The aqueous layer was discarded, the organic layer was concentrated at reduced pressure (40° C., 300 to 50 mbar), the resulting oil solidified upon standing at room temperature.

To facilitate the transition to Step 2, a solvent switch may be performed from MTBE/EtOH to the solvent used in the second step (acetic acid) instead of completely removing the solvent and letting the oil solidify.

The same procedure was repeated with varying amounts of the base at various temperatures. The results are presented in Tables 3 and 4.

TABLE 3

Effect of Base Amount on SUMO-1/SUMO-1 Isomer Ratio

| Experiment # | Amount of $Na_2CO_3$ (eq) | pH | Yield * | SUMO-1/Isomer Ratio |
|---|---|---|---|---|
| Han-601 | 1.20 | 8.9 | 83.9 | 5 |
| Han-602 | 1.05 | 8.1 | 82.4 | 5.4 |
| Han-603 | 1.1 | 8.5 | 83.5 | 5.9 |

* As area % in HPLC

TABLE 4

Effect of Temperature on SUM0-1/Isomer Ratio (1.1 Eq of Na2C03)

| Experiment # | Temperature (° C.) | Yield * | SUMO-1/Isomer Ratio |
|---|---|---|---|
| Han-603 | 0 | 83.5 | 5.9 |
| Han-606 | −5 | 85.0 | 6.3 |
| Han-607 | −8 | 85.2 | 6.5 |
| Han-609 | −10 | 82.8 | 6.4 |

* As area % in HPLC

Examples for SUMO-2 Preparation Step

Example 3. Preparation of SUMO-2 in 1-Stage Reaction 1 eq. of SUMO-1 and 1 eq. of 1,3-cyclohexanedione were dissolved in acetic acid. Four catalysts (2 Pd/C and 2 Raney-nickel) were used on a small scale at 25° C. to 40° C. and 1-5 bar hydrogen pressure. With all 4 catalysts, SUMO-1 was eventually completely consumed; the reaction, however, was a little faster on the Pd/C catalysts than the Raney-nickel ones. At the low temperature, an intermediate with the following formula was formed,

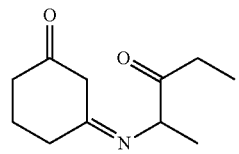

characterized by a late eluting peak (9.6 min). When the reaction temperature was raised to 100° C., the late eluting peak started to decrease and SUMO-2 increased.

Example 4. Preparation of SUMO-2 Intermediate Using Pd/C Catalyst

SUMO-1 (1 eq.) and 1,3-cyclohexanedione (1 eq.) were dissolved in ethyl acetate/acetic acid (3:1) and 0.1 g/g Pd/C catalyst was added. The reaction was carried out at 1 bar of hydrogen at 50° C., and the conversion to the intermediate worked smoothly.

Example 5. Preparation of SUMO-2 Using Pd/C Catalyst in a 2-Stage Reaction

SUMO-1 in acetic acid (—10 w %) was charged into the autoclave, followed by 0.1 g/g Pd/C. The autoclave was pressurized to 3 bar with hydrogen. The reaction mixture was stirred at 25° C. until hydrogen consumption indicated complete conversion (~15 h). Then the catalyst was filtered off and 1,3-cyclohexanedione (1.1 eq) in some acetic acid (~50 w %) was added. The reaction mixture was heated to 110° C. jacket temperature (~100° C.-105° C. internal) and stirred until GC shows complete conversion (~5 h). Then the reaction mixture was cooled to 50° C. and part of the acetic acid was removed under reduced pressure (to ca. 3 g/g SUMO-1). This solution was slowly added into 3 times the weight of chilled (2° C.) water. After aging at 2° C. for 1 h, the product was isolated by filtration, washed with water and dried at 40° C. in vacuo to yield 54% SUMO-2 crude with −11% isomer. SUMO-2 crude was suspended in methanol/water=2/1 (v/v) (10 w %) at room temperature. Then the reaction mixture was heated to 75° C. jacket temperature, and a clear solution was obtained somewhere between 60 and 70° C. internal temperature. Then the reaction mixture was cooled to 0° C. within 2 hours and the reaction mixture was aged at 0° C. for 1 hour. Then the product was isolated by filtration, washed with methanol/water and dried at 40° C. in vacuo to yield 76% SUMO-2 with −2% Isomer from SUMO-2 crude, or 41% yield overall.

Example 6. Preparation of SUMO-2 Using Ra Ni Catalyst in a 2-Stage Reaction

SUMO-1 in acetic acid (~10%) was reacted with 1,3-cyclohexadione in the presence of 0.3 g/g Raney nickel catalyst at 25° C. under 3 bar of hydrogen. The catalyst was filtered off and the temperature was increased to 100° C. A 42.4% yield of SUMO-2 was obtained.

Example 7. Preparation of SUMO-2 Using Zn/HOAc 17.5 g (156.5 mmol) 1,3-cyclohexanedione and 16.8 g (144 mmol) SUMO-1 (PER-3143-1) were dissolved in 156 g acetic acid at room temperature. 20.5 g (313 mmol) powder Zn was added in small portions over a period of ~1 hour, and the mixture was stirred at reflux for 1 hour. The suspension was cooled down to room temperature. Then the suspension was filtered off via celite and the celite was washed with 40 g acetic acid. The yellow brown solution was concentrated in vacuum to 50 g solution and then it was added over a period of 15 minutes to 150 g cold water (2° C.). A slightly brown solid was precipitated. The suspension was further stirred for 1 hour at 2° C. and filtered off. The filter cake was washed twice with 40 ml cold water. The slightly brown solid was dried in vacuum at 40° C.:

Yield: 19.7 g (77%)

Example 8. Preparation of SUMO-2 Using Zn/HOAc in a 2-Stage Reaction 1,3-cyclohexanedione and SUMO-1 were dissolved at room temperature in acetic acid. Then powder Zn was added in small portions. The mixture was then stirred at reflux. Reaction mixture was worked up as described in Example 7.

SUMO-1 was dissolved at room temperature in acetic acid. Powder Zn was added in small portions. The mixture was then stirred at reflux. Zn was then removed by filtration. 1,3-cyclohexanedione was added. The reaction mixture was stirred at reflux. The reaction mixture was worked up as described in Example 7.

Results:

| Entry | SUMO-2 % area count | rrt = 0.74 % area count | rrt = 0.88 % area count | Rrt = 0.99 % area count | SUMO-2 isomer % area count | SUMO-2: SUMO-2 isomer ratio |
|---|---|---|---|---|---|---|
| Hil-3194 | 80.3 | 0.73 | 0.62 | 0.11 | 18.0 | 4.7:1 |
| Hil-3195 | 84.3 | 0.46 | 0.42 | Not detected | 14.7 | 5.7:1 |

Example 9. Purification of SUMO-2

1. SUMO-2 was prepared as disclosed in Example 5. After the removal of the acetic acid, the reaction mixture was divided into four parts.
   a. The warm solution of SUMO-2 in acetic acid was dosed slowly into cold water,
   b. The second part was crystallized similar to the re-crystallization procedure by dissolving SUMO-2 In residual acetic acid, methanol and water at 70° C. and slowly cooling to 2° C., improving the depletion of the undesired isomer.
   c. In the third part, water was added into the cold solution of SUMO-2 in residual acetic acid and methanol.
   d. The fourth part finally was performed by adding cold water to the ~50° C. warm solution of SUMO-2 in residual acetic acid.

TABLE 5

| | Purification SUMO-2 | | | |
|---|---|---|---|---|
| | Treatment (a) | Treatment (b) | Treatment (c) | Treatment (d) |
| Yield (%) | 56 | 32.7 | 35.1 | 57.2 |
| SUMO-2 (%) | 83.1 | 95.1 | 93.8 | 82.5 |
| SUMO-2 Isomer (%) | 15.7 | 4.67 | 5.99 | 16.5 |

2. First recrystallization: 18 g of crude SUMO-2 from Example 7 was dissolved in 162 g MeOH/water (2/1; v/v %) at 75° C. and the solution was cooled down to 0° C. over a period of 2 h. The suspension was stirred for 1 h at 0° C. and filtered off. The filter cake was washed twice with 50 ml MeOH/water (2/1; v/v %) and dried in vacuum at 40° C. Total yield: 12.8 g.

3. Second re-crystallization: 12.5 g of SUMO-2 obtained after the first re-crystallization was dissolved in 120 g MeOH/water (2/1; v/v %) at 75° C. and the solution was cooled down to 0° C. over a period of 2 hours. The suspension was stirred for 1 hour at 0° C. and filtered off. The filter cake was washed twice with 35 ml MeOH/water (2/1; v/v %) and dried in vacuum at 40° C. Overall yield of 10.5 g (45%) was achieved.

Examples for SUMO-3 Preparation Step

Example 10. Preparation of N-Hydroxymethyl SUMO-2

SUMO-2 is reacted with formaldehyde in the presence of aqueous acid (aq. HCl, aq. HOAc, or aq. H2SO4) to produce N-hydroxymethyl-SUMO-2 of the following structure:

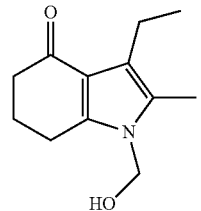

Example 11. Preparation of SUMO-3 by Reacting SUMO-2 With Bismorphomethane

The reaction of bismorpholinomethane with SUMO-2 was conducted with different solvents and acids: ethanol, ethanol/HCl and acetic acid, each at elevated temperature. The neutral conditions in ethanol and without acid showed virtually no reaction after 2 hours. In ethanol with hydrochloric acid ~10% area count of SUMO-3 was formed after 2 hours. In acetic acid after 2 h, ~50% area count of SUMO-3 was formed and ~25% area count of SUMO-2 remained.

TABLE 7

| The reaction of bismorpholinomethane with SUM0-2 under different solvents | | | |
|---|---|---|---|
| Experiment # | Reaction Temp (° C.) | Amount of Mannich Reactant (Eq) | Solvent |
| Hil-3238 | 80 | 1 | EtOH |
| Hil-3239 | 80 | 1 | EtOH/HCl |
| Hil-3240 | 80 | 1 | AcOH |

Example 12

Preparation of SUMO-3 by Reacting SUMO-2 With Bismorpholinomethate a. SUMO-2 was Dissolved in Acetic Acid and Heated to 65° C.

Bismorpholinomethane (1.5 eq) was dosed over ~30 minutes; the progress of the reaction was followed by HPLC. After 3 hours, the reaction temperature was increased to 80° C. After 3 hours at 80° C., 9% area count of compound at rrt=0.82 was left, 44% area count of SUMO-3 formed and 25% area count of SUMO-2 was left (and <1% area count of methylene-SUMO-2). The reaction mixture was stirred at 80° C. overnight and after 18 hours at 80° C., the following HPLC was observed: <1% area count of compound at rrt=0.82, 59% area count of SUMO-3, 20% area count of SUMO-2 and 7% area count of methylene-SUMO-2.

b. Incremental Addition of Bismorpholinomethane 2.0 eq of bismorpholinomethane was charged to SUMO-2 dissolved in acetic acid at 80° C. directly. At this temperature, SUMO-3 already started to appear from the first HPLC in significant amounts and the intermediate rrt=0.82 was formed only in smaller amounts. After 3 hours, another 0.5 eq of bismorpholinomethane was charged. After 20 hours, the reaction was stopped with ~62% area count of SUMO-3, <1% area count of compound at rrt=0.82, ~15% area count of SUMO-2 and ~15% area count of methylene-SUMO-2.

c. SUMO-2 was dissolved in acetic acid and heated to 50° C. The reaction was pushed to 90% conversion, which was achieved by starting out with 2.5 eq and charging another 0.5 eq of bismorpholinomethane after a few hours. With less than 11% SUMO-2 (and >80% of the intermediate rrt=0.82) left, the temperature was increased to 80° C., and the reaction mixture was stirred for 10 hours. Surprisingly, after 10 hours at 80° C. the reaction mixture contained 59% SUMO-3, 3% rrt=0.82 and 20% SUMO-2.

d. SUMO-2 was Dissolved in Acetic Acid and Heated to 50° C.

Bismorpholinomethane was charged at 50° C. (2 eq). After 2 hours, the temperature was raised to 80° C. After 2 hours aging at 80° C., another 1 eq of bismorpholinomethane was added, followed by 10 hours aging at 80° C. Only 11% of residual SUMO-2 remained; the yield of SUMO-3 was close to 60% area count.

TABLE 8

Preparation of SUM0-3 with Bismorpholinomethane:
Temperature and Charging Conditions

| Experiment # | Initial Temp ° C. | Ramp Temp ° C. | Solvent | Initial Amount of Mannich Reagent (Eq) | Ramp Amount of Mannich Reagent (Eq) |
|---|---|---|---|---|---|
| Hil-3243 | 65 | 80 | AcOH | 1.5 | n/a |
| Hil-3245 | 80 | n/a | AcOH | 2 | 0.5 |
| Han-622 | 50 | 80 | AcOH | 2.5 | 0.5 |
| Hil-3250 | 50 | 80 | AcOH | 2 | 1 |

Example 13. Work-Up of SUMO-3 after the Reaction of SUMO-2 with Bismorpholinomethane To remove impurities, such as methylene-SUMO-2 and SUMO-2, most of the acetic acid was distilled off and water was added. Another acid such as HCl and $H_2SO_4$ can be used to adjust the pH of the aqueous solution. SUMO-3 remained in solution whereas the impurities crashed out as a slightly sticky solid and was filtered off. Then the reaction mixture was warmed to 40° C., MTBE was added and the pH was adjusted to >7 with sodium hydroxide. Afterwards the phases were separated and the aqueous layer was extracted a second time with MTBE. The MTBE phase was concentrated and SUMO-3 free base was crystallized upon cooling at 50.8% yield (89.8% purity).

Alternatively, after the filtration of the crashed-out impurities as described above, the pH-adjustment of the acidic solution was performed as follows: charge the acidic solution, warm to 45° C., charge charcoal, charge MTBE, charge ethanol and then dose sodium hydroxide to liberate the SUMO-3 free base. Charcoal was added to bind the semi-solid by-product and facilitate its removal by filtration and washed afterwards with MTBE/EtOH solvent. The combined MTBE/EtOH was concentrated to produce.SUMO-3 free base crystals.

Example 14. SUMO-3 Free Base

SUMO-3 free base was crystallized from MTBE/EtOH mixture or from EtOH. 45% overall yield was obtained with high purity (98%).

Example 15. Molindone Hydrochloride Formation

SUMO-3 free base was converted into the hydrochloride salt with HCl/EtOH (i-PrOH) and crystallized from ethanol or isopropanol. Molindone HCl was obtained with high yield (95%) and high purity (99.5%).

The invention claimed is:

1. A composition consisting of molindone or its pharmaceutically acceptable salts as the sole active ingredient and comprising formaldehyde, (Z)—N-[(2Z)-2-(hydroxyimino)pentan-3-ylidene]hydroxylamine, (E)-N-ethylidenehydroxylamine, and (2Z)-2-(hydroxyimino)propan-1-ol.

2. The composition of claim 1, comprising less than 1.5 micrograms per human daily dose of each of formaldehyde, (Z)—N-[(2Z)-2-(hydroxyimino)pentan-3-ylidene]hydroxylamine, (E)-N-ethylidenehydroxylamine, (2Z)-2-(hydroxyimino)propan-1-ol.

3. A composition comprising molindone or its pharmaceutically acceptable salts as the sole active ingredient, formaldehyde, (Z)—N-[(2Z)-2-(hydroxyimino)pentan-3-ylidene]hydroxylamine, (E)-N-ethylidenehydroxylamine, and (2Z)-2-(hydroxyimino)propan-1-ol.

4. The compositions of claim 3, comprising less than 1.5 micrograms per human daily dose of each of formaldehyde, (Z)—N-[(2Z)-2-(hydroxyimino)pentan-3-ylidene]hydroxylamine, (E)-N-ethylidenehydroxylamine, (2Z)-2-(hydroxyimino)propan-1-ol.

5. A composition comprising molindone or its pharmaceutically acceptable salts as the sole active ingredient and formaldehyde.

6. A composition comprising molindone or its pharmaceutically acceptable salts as the sole active ingredient, formaldehyde, and (Z)—N-[(2Z)-2-(hydroxyimino)pentan-3-ylidene]hydroxylamine.

7. A composition comprising molindone or its pharmaceutically acceptable salts as the sole active ingredient, formaldehyde, (Z)—N-[(2Z)-2-(hydroxyimino)pentan-3-ylidene]hydroxylamine, and (E)-N-ethylidenehydroxylamine.

8. A composition comprising molindone or its pharmaceutically acceptable salts as the sole active ingredient and (Z)—N-[(2Z)-2-(hydroxyimino)pentan-3-ylidene]hydroxylamine.

9. A composition comprising molindone or its pharmaceutically acceptable salts as the sole active ingredient, (Z)—N-[(2Z)-2-(hydroxyimino)pentan-3-ylidene]hydroxylamine, and (E)-N-ethylidenehydroxylamine.

10. A composition comprising molindone or its pharmaceutically acceptable salts as the sole active ingredient, (Z)—N-[(2Z)-2-(hydroxyimino)pentan-3-ylidene]hydroxylamine, (E)-N-ethylidenehydroxylamine, and (2Z)-2-(hydroxyimino)propan-1-ol.

11. A composition comprising molindone or its pharmaceutically acceptable salts as the sole active ingredient and (E)-N-ethylidenehydroxylamine.

12. A composition comprising molindone or its pharmaceutically acceptable salts as the sole active ingredient, (E)-N-ethylidenehydroxylamine, and (2Z)-2-(hydroxyimino)propan-1-ol.

13. A composition comprising molindone or its pharmaceutically acceptable salts as the sole active ingredient and (2Z)-2-(hydroxyimino)propan-1-ol.

* * * * *